(12) United States Patent
Krager et al.

(10) Patent No.: US 8,062,609 B2
(45) Date of Patent: Nov. 22, 2011

(54) FLOW CYTOMETER AND FLUIDIC LINE ASSEMBLY WITH MULTIPLE INJECTION NEEDLES

(75) Inventors: Jarden E. Krager, Cedar Park, TX (US); William R. Deicher, Austin, TX (US); Adam Richard Schilffarth, Cedar Park, TX (US); Paul Pempsell, Bedford, TX (US); Wayne D. Roth, Leander, TX (US)

(73) Assignee: Luminex Corporation, Austin, TX (US)

( * ) Notice: Subject to any disclaimer, the term of this patent is extended or adjusted under 35 U.S.C. 154(b) by 1013 days.

(21) Appl. No.: 11/938,457

(22) Filed: Nov. 12, 2007

(65) Prior Publication Data

US 2008/0113447 A1 May 15, 2008

Related U.S. Application Data

(60) Provisional application No. 60/865,277, filed on Nov. 10, 2006.

(51) Int. Cl.
*G01N 21/01* (2006.01)
(52) U.S. Cl. .......... 422/508; 422/73; 422/145; 422/213; 422/220; 422/278; 422/501; 422/502; 422/504; 422/505; 422/515; 422/524; 436/180; 356/335; 324/71.4
(58) Field of Classification Search ............... 422/100, 422/501, 524, 515, 73, 278, 213, 220, 145, 422/508, 500, 502, 504, 505; 436/180; 356/335; 324/71.4
See application file for complete search history.

(56) References Cited

U.S. PATENT DOCUMENTS

| 4,352,558 A | 10/1982 | Eisert |
| 5,736,330 A | 4/1998 | Fulton |
| 5,981,180 A | 11/1999 | Chandler et al. |

(Continued)

FOREIGN PATENT DOCUMENTS

EP 0478392 4/1992

(Continued)

OTHER PUBLICATIONS

Lee et al., "Micromachine-based multi-channel flow cytometers for cell/particle counting and sorting," Journal of Micromechanics & Microengineering, vol. 15, Mar. 2005, pp. 447-454.

(Continued)

*Primary Examiner* — Jill Warden
*Assistant Examiner* — Shogo Sasaki
(74) *Attorney, Agent, or Firm* — Fulbright & Jaworski LLP (57) ABSTRACT

A flow cytometer is provided which includes an interrogation flow cell and a plurality of assay fluidic lines extending into the interrogation flow cell. A method of operating such a flow cytometer includes priming the interrogation flow cell with a sheath fluid and injecting different assay fluids into a flow of the sheath fluid through the plurality of fluidic lines. A fluidic line assembly is provided which includes a plurality of capillary tubes coupled to a base section configured for coupling to an interrogation flow cell assembly of a flow cytometer. The capillary tubes are dimensionally configured such that when the fluidic line assembly is arranged within the flow cytometer and fluid is dispensed from one or more of the capillary tubes at a given pressure differential with respect to an encompassing sheath fluid within the interrogation flow cell the fluid is substantially centrally aligned within the interrogation flow cell.

15 Claims, 6 Drawing Sheets

U.S. PATENT DOCUMENTS

| | | | |
|---|---|---|---|
| 6,046,807 A | 4/2000 | Chandler | |
| 6,057,107 A | 5/2000 | Fulton | |
| 6,139,800 A | 10/2000 | Chandler | |
| 6,268,222 B1 | 7/2001 | Chandler et al. | |
| 6,315,952 B1 | 11/2001 | Sklar et al. | |
| 6,366,354 B1 | 4/2002 | Chandler | |
| 6,411,904 B1 | 6/2002 | Chandler | |
| 6,449,562 B1 | 9/2002 | Chandler et al. | |
| 6,514,295 B1 | 2/2003 | Chandler et al. | |
| 6,524,793 B1 | 2/2003 | Chandler et al. | |
| 6,528,165 B2 | 3/2003 | Chandler | |
| 6,638,481 B2 | 10/2003 | Sklar | |
| 2005/0036921 A1* | 2/2005 | Nagasawa et al. | 422/130 |

FOREIGN PATENT DOCUMENTS

| | | |
|---|---|---|
| EP | 1481724 | 12/2004 |
| EP | 1356859 | 8/2008 |
| WO | 00/49385 | 8/2000 |

OTHER PUBLICATIONS

Mandy et al., "Principles of Flow Cytometry," Transfusion Science, vol. 16, No. 4, Dec. 1995, pp. 303-314.

International Search Report & Written Opinion, PCT/US2007/084417, mailed May 27, 2008.

* cited by examiner

FLOW CYTOMETER AND FLUIDIC LINE ASSEMBLY WITH MULTIPLE INJECTION NEEDLES

PRIORITY CLAIM

This application claims priority to U.S. Provisional Application No. 60/865,277 filed Nov. 10, 2006.

BACKGROUND OF THE INVENTION

1. Field of the Invention

This invention generally relates to fluid flow devices and, more specifically, to the use of multiple sample injection needles in a flow cytometer.

2. Description of the Related Art

The following descriptions and examples are not admitted to be prior art by virtue of their inclusion within this section.

Spectroscopic techniques are widely employed in the analysis of chemical and biological systems. Most often, these techniques involve measuring the absorption or emission of electromagnetic radiation by the material of interest. One such application is in the field of microarrays, which is a technology exploited by a large number of disciplines including the combinatorial chemistry and biological assay industries. Luminex Corporation of Austin, Tex., has developed a system in which biological assays are performed on the surface of variously colored fluorescent microspheres. Contemporary flow cytometers using these microspheres can test for tens to over one hundred different analytes in a biological sample and future increases are probable. While the ability to test for large numbers of analytes has improved, the fluid handling of a sample for examination has surfaced as an impediment to productivity.

In a typical flow cytometer, a sample is aspirated into the flow cytometer using a positive displacement pump and a network of tubing and valves. The sample is then injected through a sample injection needle into an interrogation flow cell (e.g., cuvette) which hydrodynamically focuses the sample via a sheath fluid. This focusing technique serves to separate particles for individual interrogation and confines the particles to a known location in the flow cell. In many cases, the sample injection needle is centrally positioned within the interrogation flow cell such that a sample may be introduced and focused within a central portion of an encompassing sheath fluid. Such a configuration has generally limited flow cytometers to have only one sample injection needle within the interrogation flow cell as multiple injection needles would constitute at least some of the needles to be off center, hindering the focus of fluid dispensed therefrom. As a consequence, throughput of flow cytometers is generally limited. In addition, a single injection needle configuration requires assays to be fully prepared prior to being injected into an interrogation flow cell, increasing time and money for analyzing a sample and further limiting the application of the flow cytometers to fully prepared assays.

SUMMARY OF THE INVENTION

The following descriptions of various embodiments of flow cytometers, fluidic line assemblies, and methods are not to be construed in any way to limit the subject matter of the claims.

An embodiment of a flow cytometer includes an interrogation flow cell and a fluid handling system which includes a sheath fluidic line for supplying a sheath fluid to the interrogation flow cell and a plurality of assay fluidic lines extending into the interrogation flow cell for introducing one or more assay fluids into a flow of the sheath fluid within the interrogation flow cell.

An embodiment of a fluidic line assembly includes a base section configured for coupling to an interrogation flow cell assembly of a flow cytometer and a plurality of capillary tubes coupled to the base section. The capillary tubes are dimensionally configured such that when the fluidic line assembly is arranged within the flow cytometer and fluid is dispensed from one or more of the capillary tubes at a given pressure differential with respect to an encompassing sheath fluid flow within an interrogation flow cell of the interrogation flow cell assembly the fluid is substantially centrally aligned within the interrogation flow cell.

An embodiment of a method for operating a flow cytometer with multiple assay fluidic lines includes priming an interrogation flow cell of the flow cytometer with a sheath fluid and injecting different assay fluids into a flow of the sheath fluid within the interrogation flow cell through the separate fluidic lines.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Figure 1:
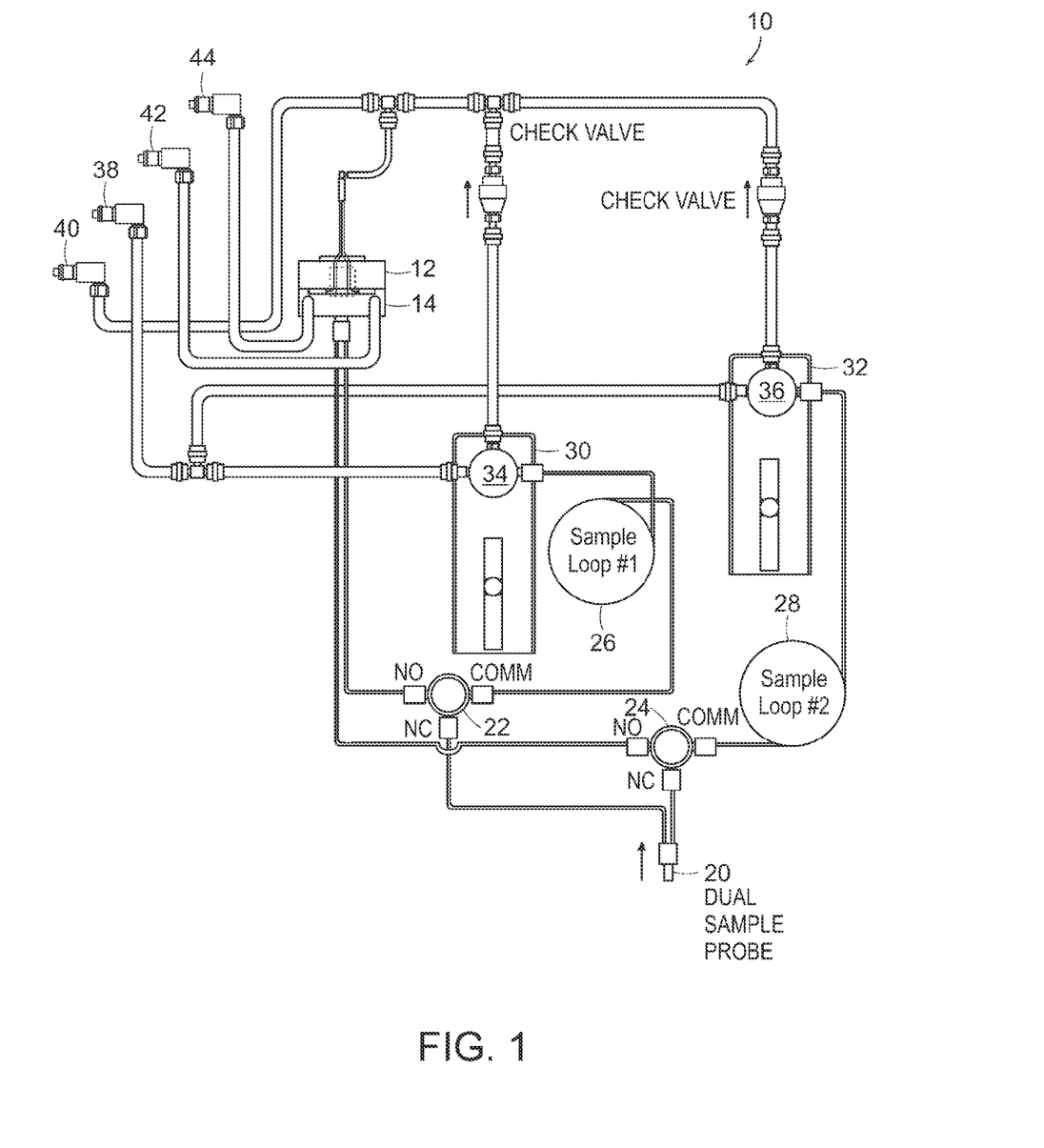
FIG. 1 is a fluid interconnect diagram of a flow cytometer.
Figure 2:
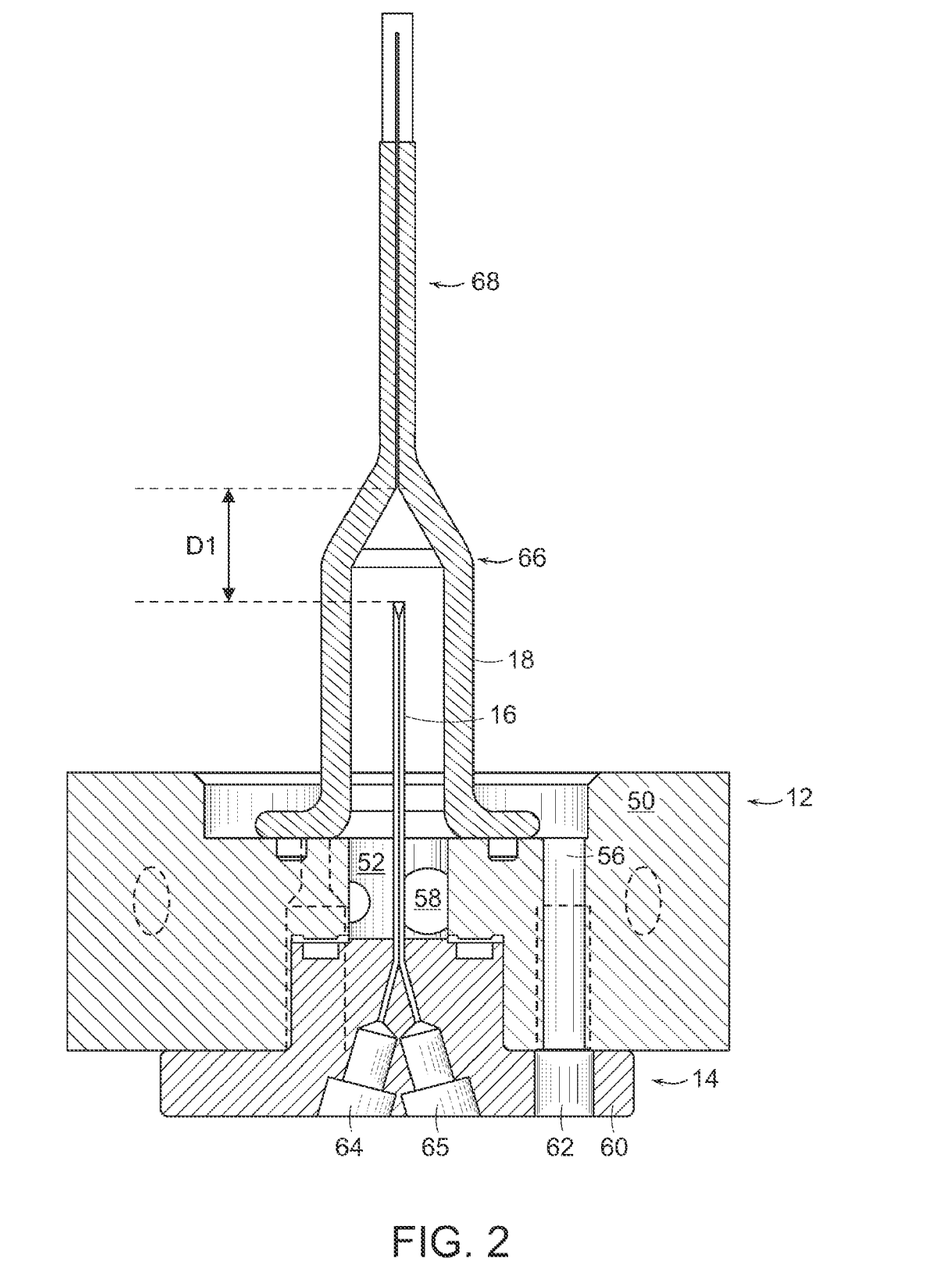
FIG. 2 illustrates a cross-sectional view of an exemplary interrogation flow cell assembly and fluidic line assembly coupled together.
Figure 3A:
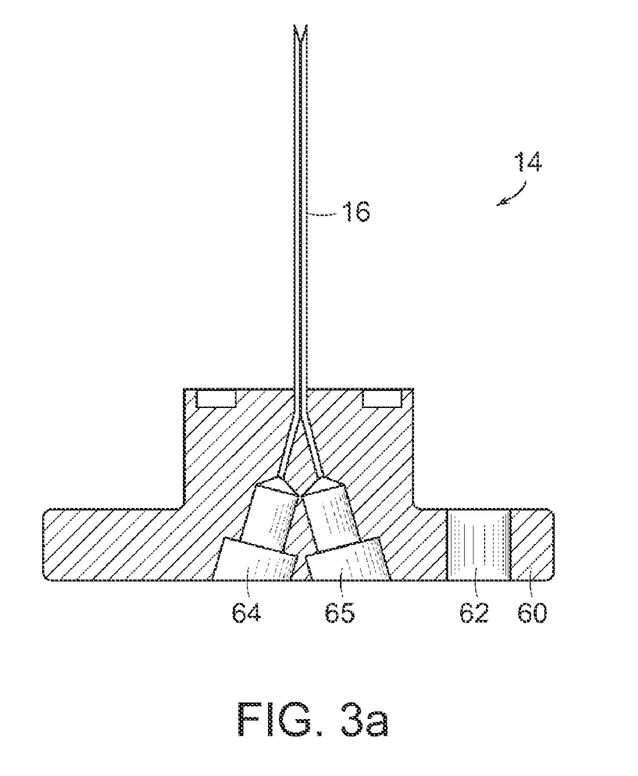
FIGS. 3a and 3b respectively illustrate cross-sectional and perspective view of the fluidic line assembly depicted in FIG. 2.
Figure 3B:
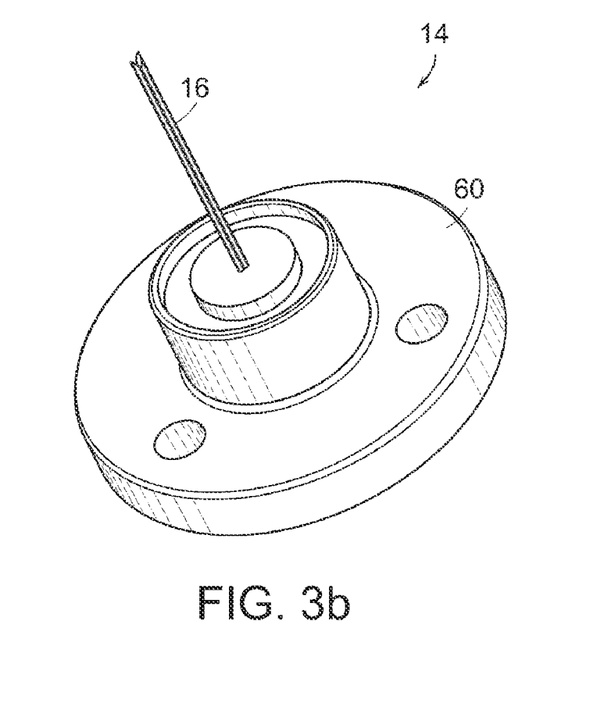
Figure 4:
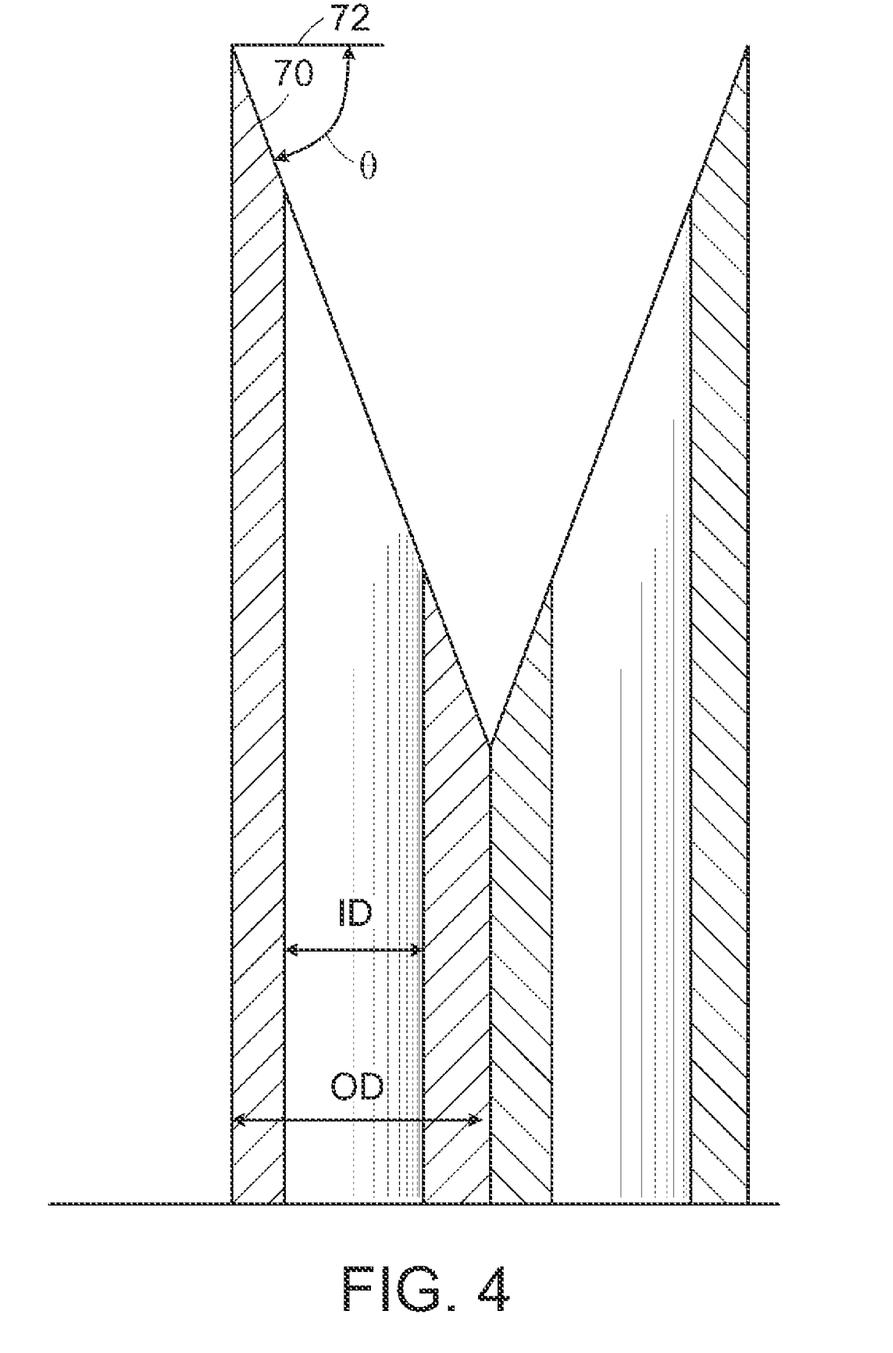
FIG. 4 is a magnified view of distal ends of the multiple injection needles of the fluidic assembly depicted in FIGS. 3a and 3b.
Figure 5A:
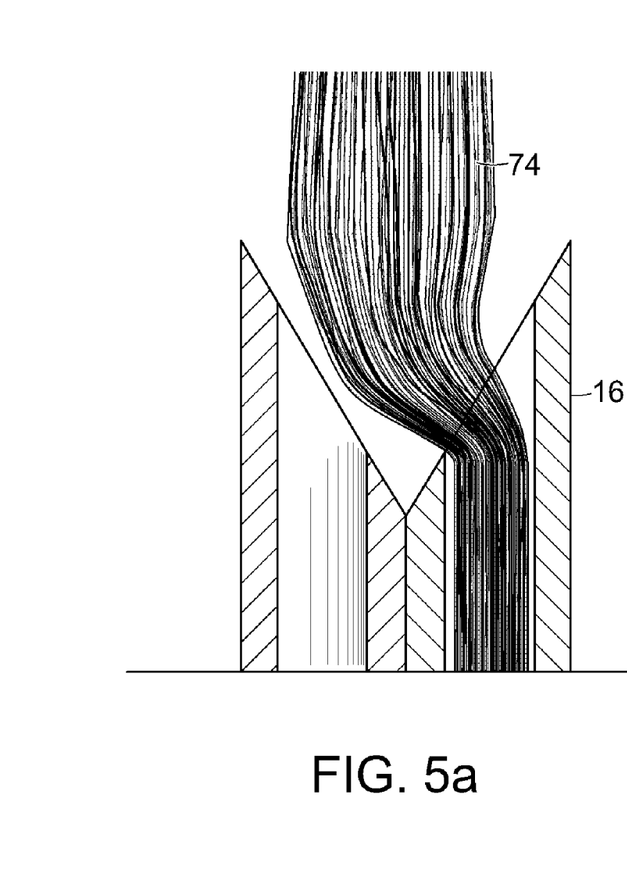
FIGS. 5a and 5b illustrate flow patterns of assay fluids dispensed from one or more of the assay fluidic lines described herein.
Figure 5B:
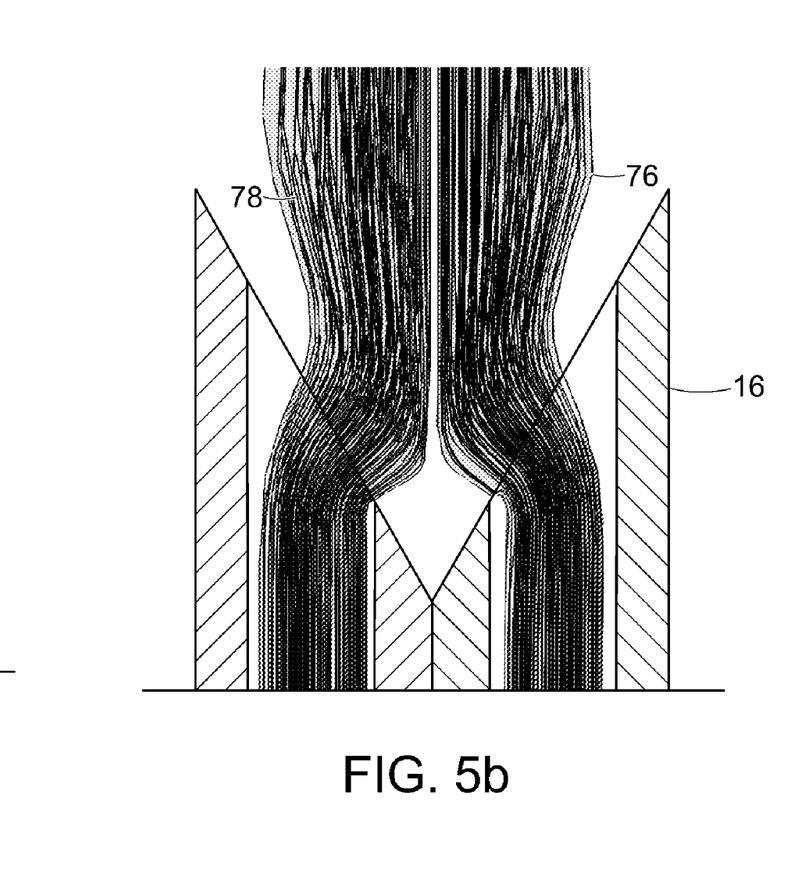
Figure 6:
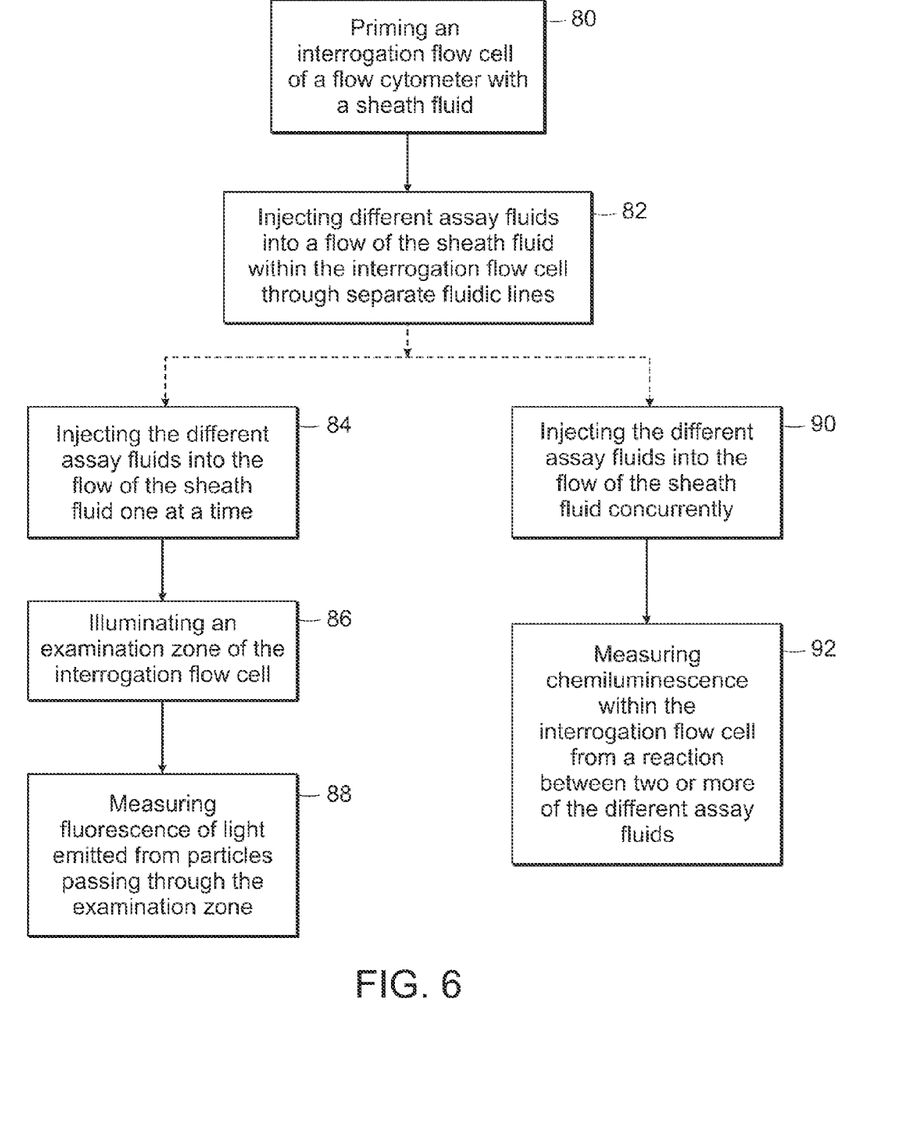
FIG. 6 is a flowchart outlining a method for operating the fluid diagram of FIG. 2.

Turning to the drawings, exemplary flow cytometers, fluidic line assemblies and methods for operating a flow cytometer are shown. In particular, FIG. 1 illustrates a fluid interconnect diagram of an exemplary flow cytometer including interrogation flow cell assembly 12 and fluidic line assembly 14 coupled thereto. FIG. 2 illustrates an exemplary magnified view of such assemblies showing fluidic line assembly 14 having a plurality of assay fluidic lines 16 extending into interrogation flow cell 18 when the assemblies are coupled together. FIGS. 3a and 3b respectively illustrate cross-sectional and perspective views of fluidic line assembly 14 and FIG. 4 illustrates a magnified view of the distal ends of assay fluidic lines 16. FIGS. 5a and 5b illustrate exemplary flow patterns of fluid dispensed from assay fluidic lines 16. FIG. 6 illustrates a flow chart of an exemplary method for operating the flow cytometers described herein. It is noted that the figures are not necessarily drawn to scale. In particular, the scale of some elements in some of the figures may be greatly exaggerated to emphasize characteristics of the elements. In addition, it is further noted that the figures are not drawn to the same scale. Elements shown in more than one figure that may be similarly configured have been indicated using the same reference numerals.

As shown in FIG. 1, flow cytometer 10 includes valves, pumps and several fluid pathways in addition to interrogation flow cell assembly 12 and fluidic line assembly 14. In particular, flow cytometer 10 includes sample input 20 coupled via fluid pathways to valves 22 and 24. Embodiments of the sample input 20 include using a single sample probe with two fluid channels, two sample probes, and a single sample probe with a 'Y' splitter connecting multiple subsystems to the single probe. In any case, each of valves 22 and 24 are shown to have three, selectable positions labeled "NO," "NC," and "COMM," referring respectively to the conventional valve nomenclature of "normally open," "normally closed," and "common." Valves 22 and 24 are respectively coupled to sample loops 26 and 28 through their COMM ports and to interrogation flow cell assembly 12 via ports NO.

Sample loops 26 and 28 are respectively coupled to pumps 30 and 32. As discussed in more detail below in reference to FIG. 5 regarding methods for operating the flow cytometers described herein, pumps 30 and 32 may be used to draw (i.e., aspirate) samples from sample input 20 into sample loops 26 and 28 and further propel the samples from the sample loops into interrogation flow cell assembly 12. The action of injecting the samples into interrogation flow cell assembly 12 may be performed at different times or at the same time, depending on the assay being analyzed. As shown with pumps 30 and 32 in FIG. 1, flow cytometer 10 may include distinct pumps respectively coupled to assay fluidic lines 16 for respectively injecting assay fluids into the interrogation flow cell. In other embodiments, however, more than one of assay fluidic lines 16 may be coupled to a single pump within flow cytometer 10. In addition or alternatively, flow cytometer 10 may, in some cases, include multiple pumps coupled to one of assay fluidic lines 16.

In any case, pumps 30 and 32 may include 3-position valves 34 and 36 to enable selectable communication with sheath fluid input 38 and waste outlet 40. FIG. 1 also illustrates interrogation flow cell assembly 12 coupled to sheath fluid input 42 and waste outlet 44. As set forth in more detail below, the flow cytometers described herein are equipped with photodetection systems for measuring light radiation from examination zones of the interrogation flow cells. An exemplary photodetection system, however, is not illustrated in FIG. 1 such that the fluid interconnections of flow cytometer 10 may be emphasized. It is noted that the fluidic path diagram of FIG. 1 is exemplary. Alternative arrangements of components and/or alternative selections of components (such as the number of pumps coupled to assay fluidic lines 16 as described above) may be considered for the flow cytometers described herein.

FIG. 2 illustrates an exemplary magnified view of interrogation flow cell assembly 12 and fluidic line assembly 14 coupled thereto. As shown, base sections 50 and 60 of interrogation flow cell assembly 12 and fluidic line assembly 14 are configured for coupling together such that plurality of assay fluidic lines 16 may extend into interrogation flow cell 18. In particular, base section 50 of interrogation flow cell assembly 12 includes channel 52 aligned with the opening of interrogation flow cell 18 for receiving assay fluidic lines 16. The manner of coupling interrogation flow cell assembly 12 and fluidic line assembly 14 may include any known means, including but not limited to the use of screws, o-rings, adhesive, etc. As shown in FIG. 2, base section 60 of fluidic line assembly 14 includes ports 64 and 65 respectively coupled to individual assay fluidic lines 16. In some embodiments, ports 64 and 65 may be coupled to separate fluidic lines of a flow cytometer (e.g., lines of flow cytometer 10 respectively connected to valves 22 and 24). In other embodiments, one or more of ports 64 and 65 may be coupled to multiple fluidic lines of a flow cytometer. In either case, each of assay fluidic lines 16 may be the terminus of completely separate sample aspiration and injection subsystems (i.e., regardless of the number of pumps coupled to the fluidic lines). As a consequence, fluidic line assembly 14 may be configured to supply different assay fluids into interrogation flow cell 18, either at the same time or different times.

In addition to providing a manner for suspending the plurality of assay fluidic lines 16 within interrogation flow cell 18, bases 50 and 60 respectively include channels 56 and 62 aligned for receiving a sheath fluid. Although not shown in the cross-sectional view of FIG. 2, channel 56 is configured to route fluid to opening 58 within channel 52. In this manner, sheath fluid may be input around the plurality of assay fluidic lines 16 via channels 62, 56 and 52. Since the surface of base 60 at which the fluidic lines 16 are coupled seals channel 58 and since interrogation assembly 12 is sealingly coupled to base 50, the sheath fluid flows through interrogation flow cell 18. It is noted that several different configurations of bases 50 and 60 and channels 52, 58 and 62 may be considered for the systems and methods described herein and, consequently, the systems and methods are not limited to the depiction of FIG. 2.

The term "interrogation flow cell," as used herein, may generally refer to an analysis vessel having at least a portion of which is transparent. The term "cuvette" is often referenced as an interrogation flow cell of a flow cytometer and, therefore, the terms may be used interchangeably herein. As noted above, the flow cytometers described herein are equipped with photodetection systems for measuring light radiation from examination zones of interrogation flow cells and, thus, transparency of at least such sections of interrogation flow cells is needed. As shown in FIG. 2, interrogation flow cell 18 may generally include focusing section 66 for receiving sheath and assay fluids as well as for hydrodynamically focusing such fluids into capillary section 68. In general, a portion of capillary section 68 may be regarded as the examination zone of interrogation flow cell 18. As with bases 50 and 60 and channels 52, 58 and 62, different configurations of cuvettes may be considered for the systems and methods described herein and, consequently, interrogation flow cell 18 is not necessarily limited to the depiction of FIG. 2.

As set forth below, assay fluidic lines 16 are dimensionally configured such that when one or more assay fluids are dispensed therefrom at a given pressure differential with respect to a flow of sheath fluid within interrogation flow cell 18 the one or more assay fluids are substantially centrally aligned within the interrogation flow cell. Among such dimensions, the plurality of assay fluidic lines 16 may be configured to extend into focusing section 66 a spaced distance from capillary section 68, as denoted by dimensional reference D1 in FIG. 2. In some embodiments, the plurality of assay fluidic lines 16 may extend into focusing section 66 a spaced distance of less than approximately 1.0 inch from capillary section 68 or, more specifically, less than approximately 0.3 inches from capillary section 68. Larger or smaller distances may also be considered, depending on the design of the interrogation flow cell and viscosity of the sheath fluid. In particular, distance D1 may generally be configured such that the sheath fluid introduced into interrogation flow cell 18 has sufficient room to confine the one or more assay fluids introduced into the interrogation flow cell. Other dimensions of assay fluidic lines 16 configured to facilitate a substantially central flow of assay fluids within interrogation flow cell 18 are described below in reference to FIG. 4.

FIGS. 3a and 3b respectively illustrate cross-sectional and perspective views of fluidic line assembly 14. As described above, fluidic line assembly 14 includes base section 60 configured for coupling to an interrogation flow cell assembly of a flow cytometer. In addition, fluidic line assembly 14 includes a plurality of assay fluidic lines 16 coupled to base section 60. Although FIGS. 2-4 only illustrate 2 fluidic lines, the systems described herein may include any plurality of fluidic lines (i.e., two or more fluidic lines), depending on the design specifications of the flow cytometer. In correlation, base section 60 may include any plurality of separate ports coupled to assay fluidic lines 16 such that different assay fluids may be dispensed from assay fluidic lines 16 when coupled to fluidic lines of a flow cytometer. In any case, assay fluidic lines 16 may be formed of stainless steel or any standard hypodermic needle material.

As noted above, the plurality of assay fluidic lines 16 are dimensionally configured such that when fluidic line assembly 14 is arranged within a flow cytometer and one or more assay fluids are dispensed therefrom at a given pressure differential with respect to a flow of sheath fluid within an interrogation flow cell of the flow cytometer the one or more assay fluids are substantially centrally aligned within the interrogation flow cell. Such dimensional configurations may be particularly targeted at the distal ends of assay fluidic lines 16 and, thus, a magnified view of assay fluidic lines 16 are shown in FIG. 4 to distinguish such dimensions. As shown in FIGS. 2-4, the distal ends of assay fluidic lines 16 are beveled and the fluidic lines are specifically oriented such that the beveled surfaces face inward (i.e., toward each other). In general, the beveled surfaces may be angled greater than approximately 0 degrees and less than approximately 90 degrees relative to the surface of base section 60 at which assay fluidic lines 16 are coupled. FIG. 4 illustrates exemplary angle θ between beveled surface 70 and plane 72 which is parallel to the surface of base section 60 at which assay fluidic lines 16 are coupled. During the development of assay fluidic lines for the assembly described herein, it was found that angles between approximately 50 degrees and approximately 80 degrees were beneficial for facilitating a flow of the assay fluids within a central portion of an interrogation flow cell and, particularly an angle θ of approximately 70 degrees was found to be optimal when two needles were employed having the dimensions outlined below. It is noted that such an optimum angle may change when dimensions of assay fluidic lines 16 are modified and/or when more than two fluidic lines are employed.

In general, assay fluidic lines 16 may have very small bores and, thus, may in some embodiments, be referred to herein as "capillary tubes" or "needles." In particular, assay fluidic lines 16 may, for example, include inner diameters of less than approximately 0.02 inches (denoted as dimension ID in FIG. 4). The outer diameters of assay fluidic lines 16 (denoted as dimension OD in FIG. 4) may be small as well such that the fluidic lines do not occupy a substantial cross-section of an interrogation flow cell. For instance, assay fluidic lines 16 may include outer diameters of less than approximately 0.1 inches. Smaller or larger dimensions for the inner and outer diameters of assay fluidic lines 16 may be employed, depending on the design specifications of the flow cytometer and characteristics of the assay fluids. During the development of assay fluidic lines for the fluidic line assembly described herein, an inner diameter of approximately 0.01 inches and an outer diameter of approximately 0.018 inches were found to be beneficial for facilitating a flow of the assay fluids within a central portion of an interrogation flow cell when two needles were employed having the dimensions outlined herein. It is noted that such optimum diameters may change when dimensions of assay fluidic lines 16 are modified and/or when more than two fluidic lines are employed. In addition, it is noted that assay fluidic lines are not necessarily restricted to being circular and, as such, the inner and outer dimensions of the lines are not necessarily limited to diameters per se.

In some cases, assay fluidic lines 16 may include the same dimensions. In other cases, however, one or more of assay fluidic lines 16 may include different dimensions. The latter case may be particularly applicable when assay fluids of different viscosities and/or flow rates may be dispensed from the different assay fluidic lines 16. More specifically, it is speculated that the dimensions of assay fluidic lines 16 may be individually optimized for the assay fluid to be dispensed therefrom. In other embodiments, assay fluidic lines 16 may be configured to dispense assays of a similar if not the same nature and flow rate and, thus, such individual optimization may not be advantageous.

Further to the aforementioned dimensions of the individual fluidic lines, assay fluidic lines 16 may be arranged in close proximity to each other. In some embodiments, assay fluidic lines 16 may be arranged in contact with each other as shown in FIG. 4. In other cases, assay fluidic lines 16 may be spaced apart by a set distance, such as but not limited to less than approximately 0.005 inches. Smaller or larger spacings may be considered depending on the design specifications of the interrogation flow cell and the viscosities and flow rates of the assay fluids and the sheath fluid. In any case, assay fluidic lines 16 may generally be centered around a central axis of the interrogation flow cell into which they extend. Such a configuration may further insure flow/s of assay fluids dispensed therefrom are substantially centrally aligned within the interrogation flow cell. In cases in which a flow cytometer includes only two assay fluidic lines within an interrogation flow cell and the assay fluidic lines are of similar dimensions, the arrangement of the fluidic lines may be symmetrical relative to the central axis of the interrogation flow cell.

As set forth below, the multiple injection needles of the flow cytometers described herein may be used either inject assay fluids one at a time or concurrently within an interrogation flow cell. In embodiments in which assay fluids are injected one at a time, the configuration of the multiple fluidic lines extending into the interrogation flow cell may be particularly advantageous for analyzing assay samples more quickly than conventional flow cytometers. In particular, while a first sample is being injected into the interrogation flow cell, a second sample may be aspirated into its respective sample loop and prepped for injection into the interrogation flow cell after the first sample is analyzed and the interrogation flow cell is subsequently flushed. In the case of a flow cytometer having two fluidic lines, such a process may alternate between the lines for the number of samples to be analyzed. By operating separately, each sample flow path can operate more efficiently so that samples are ready for examination in the flow cell on a continuous basis at a higher rate of throughput. It is noted that such a system may accommodate flushing of the sample loops and lines subsequent to a sample being injected and, in some embodiments, flushing may occur while a different sample is injected through the other fluidic line. In alternative embodiments, the multiple fluidic lines of the flow cytometers may be used concurrently. Such an application may be particularly suitable for mixing assay fluids together for analysis, such as but not limited to an embodiment in which a chemiluminescence reaction is induced within the interrogation flow cell.

As shown in FIGS. 5a and 5b, the dimensions of assay fluidic lines 16 may facilitate one or more assay fluids dispensed therefrom to be substantially centrally aligned within an interrogation flow cell. In particular, FIG. 5a illustrates flow pattern 74 as dispensed from one of assay fluidic lines 16. In contrast, FIG. 5b illustrates combined flow patterns 76 and 78 as dispensed from both of assay fluidic lines 16. As shown in both figures, the pressure differential between the assay fluids and the encompassing sheath fluid causes the flow patterns to drift slightly inward to the central axis of the interrogation flow cell. Thereafter, the fluid flow may be hydrodynamically focused within a central portion of the interrogation flow cell.

Methods for operating a flow cytometer having multiple fluidic lines are illustrated in the flowchart depicted in FIG. 6. In particular, FIG. 6 includes block 80 in which an interrogation flow cell of a flow cytometer is primed with a sheath fluid. The method continues to block 82 in which different assay fluids are injected into a flow of the sheath fluid within the interrogation flow cell through separate fluidic lines. As noted above, such a process may include injecting the different assay fluids one at a time or concurrently. FIG. 6 illustrates both scenarios in blocks 84, 86 and 88 and blocks 90 and 92, respectively and discusses types of analysis measurements which may be suitable for each scenario. In either case, the step of injecting the different assay fluids may include injecting the different assay fluids intermittently while maintaining a flow of sheath fluid within the interrogation flow cell. In this manner, the interrogation flow cell may be flushed/washed between samples.

As shown in block 84, the different assay fluids may, in some embodiments, be injected into the flow of sheath fluid one at a time. Such an application may be particularly suitable for cases in which the assay fluids include particles tagged with fluorescent dyes to analyze the types and/or amounts of analytes within a sample. The sample may include but are not limited to bodily fluids, environmental samples, and/or biological tissues and substances. In such embodiments, the method may include illuminating an examination zone of the interrogation flow cell as noted in block 86. In particular, a flow cytometer in such cases may include an illumination subsystem configured to illuminate an examination zone of an interrogation flow cell. Such an illumination subsystem may include one or more light sources and, in some embodiments, may further include lenses and/or filters. The one or more light sources may include lasers, light emitting diodes (LEDs), arc lamps, fiber illuminators, light bulbs, and any other suitable light sources known in the art. In some cases, the light sources may be configured to emit light having one or more wavelengths. In addition to the light sources, the flow cytometer may include a detection system configured to collect light emitted and/or scattered from particles passing through the examination zone of the interrogation flow cell. More specifically, the detection system may be configured to measure the fluorescence emitted from the particles to determine the type and/or amount of analytes within a sample and, as such, the method depicted in FIG. 6 includes such a step in block 88.

The term "particle" is used herein to generally refer to microspheres, polystyrene beads, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substrates or substances known in the art. Any of such terms may be used interchangeably herein. Exemplary magnetic microspheres which may be used for the methods and systems described herein include xMAP® microspheres, which may be obtained commercially from Luminex Corporation of Austin, Tex.

In embodiments in which the different assay fluids referenced in FIG. 6 are injected into the flow of sheath fluid concurrently as noted in block 90, the method may be particularly applicable to embodiments in which a chemiluminescence reaction is induced between the different assay fluids. In particular, in such embodiments, the method may continue to block 92 to measure chemiluminescence within the interrogation flow cell from a reaction between two or more of the different assay fluids. In such cases, the term "assay fluids" may refer to sample fluids to be analyzed as well as reagents used to produce the chemiluminescence reaction. In any embodiment, the flow cytometer may include a detection system for collecting light from the reaction and measuring the chemiluminescence. The flow cytometer in such a scenario, however, does not necessarily need a light source since the chemical reaction among the different assay fluids provides light. Such a distinction, however, does not necessarily bar one from performing the processes described in blocks 90 and 92 in a flow cytometer which includes an illumination system. In any case, the detection subsystems described in reference to both scenarios may include a photodetector and any number of filters, mirrors, and lenses. The photodetectors may include APDs, a PMT, a CCD Array, or another photodetector.

It will be appreciated to those skilled in the art having the benefit of this disclosure that this invention is believed to provide systems and methods employing multiple fluidic lines within an interrogation flow cell of a flow cytometer. Further modifications and alternative embodiments of various aspects of the invention will be apparent to those skilled in the art in view of this description. For example, although the figures show the inclusion of only two assay fluidic lines, the flow cytometer, fluidic line assembly, and methods described herein may include any plurality of assay fluidic lines. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A flow cytometer, comprising:
  an interrogation flow cell comprising an examination zone
  a fluid handling system coupled to the interrogation flow cell, the fluid handling system comprising:
    a sheath fluidic line for supplying a sheath fluid to the interrogation flow cell; and
    a plurality of assay fluidic lines, each comprising a proximal end and a distal end, wherein the distal ends of the plurality of assay fluidic lines are beveled and extending into the interrogation flow cell for introducing one or more assay fluids into a flow of the sheath fluid within the interrogation flow cell, wherein the beveled surfaces of the distal ends of the plurality of assay fluidic lines face each other; and a detection system configured to collect light emitted and/or scattered from particles passing through the examination zone.

2. The flow cytometer of claim 1, wherein the plurality of assay fluidic lines are dimensionally configured to substantially centrally align one or more assay fluids dispensed within the interrogation flow cell.

3. The flow cytometer of claim 1, wherein the interrogation flow cell comprises a focusing section and a capillary section, and wherein the plurality of assay fluidic lines extend into the focusing section at a spaced distance of less than approximately 1.0 inch from the capillary section.

4. The flow cytometer of claim 1, further comprising:
an illumination system configured to illuminate the examination zone of the interrogation flow cell.

5. The flow cytometer of claim 1, wherein the detection system comprises a photodetector for measuring chemiluminescence resulting from a reaction between two or more assay fluids introduced into the interrogation flow cell.

6. The flow cytometer of claim 1, wherein the fluid handling system comprises distinct pumps respectively coupled to the plurality of assay fluidic lines for respectively injecting the one or more assay fluids into the interrogation flow cell.

7. The flow cytometer of claim 1, wherein the fluid handling system comprises a pump coupled to more than one of the plurality of assay fluidic lines for injecting at least some of the one or more assay fluids into the interrogation flow cell.

8. The flow cytometer of claim 1, wherein the fluid handling system comprises multiple pumps coupled to one of the plurality of assay fluidic lines for injecting at least some of the one or more assay fluids into the interrogation flow cell.

9. The flow cytometer of claim 1, comprising two assay fluidic lines.

10. The flow cytometer of claim 1, further comprising a fluidic line assembly, wherein the plurality of assay fluidic lines are coupled to a surface of the fluidic line assembly, and wherein one or more of the distal ends are beveled at angles between approximately 50 degrees and approximately 80 degrees relative to the surface of the fluidic line assembly to which the plurality of assay fluidic lines are coupled.

11. The flow cytometer of claim 1, wherein outer diameters of the plurality of assay fluidic lines are less than approximately 0.1 inches.

12. The flow cytometer of claim 1, wherein inner diameters of the plurality of assay fluidic lines are less than approximately 0.02 inches.

13. The flow cytometer of claim 1, wherein outer diameters of the plurality of assay fluidic lines are approximately 0.018 inches, and wherein inner diameters of the plurality of assay fluidic lines are approximately 0.01 inches.

14. The flow cytometer of claim 1, wherein the plurality of assay fluidic lines are spaced apart from each other by less than approximately 0.005 inches.

15. The flow cytometer of claim 1, wherein the plurality of assay fluidic lines comprise substantially equal dimensions.

* * * * *

UNITED STATES PATENT AND TRADEMARK OFFICE
CERTIFICATE OF CORRECTION

| | | |
|---|---|---|
| PATENT NO. | : 8,062,609 B2 | Page 1 of 1 |
| APPLICATION NO. | : 11/938457 | |
| DATED | : November 22, 2011 | |
| INVENTOR(S) | : Jarden E. Krager et al. | |

It is certified that error appears in the above-identified patent and that said Letters Patent is hereby corrected as shown below:

In claim 1, column 9, line 1, delete "extending" and insert --extend-- therefor.

Signed and Sealed this
Fourteenth Day of February, 2012

David J. Kappos
*Director of the United States Patent and Trademark Office*